(12) United States Patent
Tardy et al.

(10) Patent No.: US 7,160,259 B2
(45) Date of Patent: Jan. 9, 2007

(54) FLUID MANIPULATING SYSTEM FOR THERAPY APPARATUS

(75) Inventors: Fréderiqué Tardy, Vaulx en Velin (FR); Yves Martin, Vaulx en Velin (FR); Emmanuel Blanc, Vaulx en Velin (FR)

(73) Assignee: Technomed Medical Systems, Vauln En Velin (FR)

( * ) Notice: Subject to any disclaimer, the term of this patent is extended or adjusted under 35 U.S.C. 154(b) by 161 days.

(21) Appl. No.: 10/257,304

(22) PCT Filed: Apr. 10, 2001

(86) PCT No.: PCT/FR01/01090

§ 371 (c)(1),
(2), (4) Date: Feb. 13, 2003

(87) PCT Pub. No.: WO01/78837

PCT Pub. Date: Oct. 25, 2001

(65) Prior Publication Data

US 2003/0149360 A1    Aug. 7, 2003

(30) Foreign Application Priority Data

Apr. 12, 2000  (FR) .................. 00 04703

(51) Int. Cl.
*A61H 1/00* (2006.01)

(52) U.S. Cl. ........................................ 601/3
(58) Field of Classification Search ............ 600/437, 600/439, 2, 459; 601/2, 3; 604/6.13, 131, 604/6.09, 122, 408, 4–6, 251, 22, 30; 435/284.1; 137/1; 606/31; 206/571
See application file for complete search history.

(56) References Cited

U.S. PATENT DOCUMENTS

| | | | |
|---|---|---|---|
| 3,739,366 A * | 6/1973 | Lace | 340/606 |
| 3,777,507 A * | 12/1973 | Burton et al. | 435/284.1 |
| 4,186,565 A | 2/1980 | Toledo-Pereyra | |
| 4,401,431 A * | 8/1983 | Arp | 604/6.14 |
| 4,540,399 A * | 9/1985 | Litzie et al. | 604/6.14 |
| 4,622,032 A * | 11/1986 | Katsura et al. | 604/122 |
| 4,759,499 A * | 7/1988 | Gusinde et al. | 237/12.3 B |
| 4,874,359 A * | 10/1989 | White et al. | 604/6.09 |
| 5,086,449 A | 2/1992 | Furbee et al. | |
| 5,211,201 A * | 5/1993 | Kamen et al. | 137/1 |
| 5,403,281 A * | 4/1995 | O'Neill et al. | 604/113 |
| 5,472,876 A * | 12/1995 | Fahy | 435/284.1 |

(Continued)

FOREIGN PATENT DOCUMENTS

DE    195 09 005    4/1996

(Continued)

OTHER PUBLICATIONS

Translation of the International Preliminary Examination Report for International Application No. PCT/FR01/01090.

*Primary Examiner*—Francis J. Jaworski
(74) *Attorney, Agent, or Firm*—Welsh & Katz, Ltd.

(57) ABSTRACT

The invention concerns a fluid manipulating system, comprising a reservoir of fluid (7), a bubble trap (9) connected to the reservoir, a heat-exchanger (11) and an appliance (21) forming with the bubble trap a closed circuit of fluid, and a pump (21) circulating the fluid in the closed circuit, thereby enabling to control easily the volume of fluid in the apparatus and the temperature of said fluid. The invention is useful for manipulating coupling and cooling fluid of rectal tubes in ultrasound therapy.

12 Claims, 1 Drawing Sheet

U.S. PATENT DOCUMENTS

| | | | |
|---|---|---|---|
| 5,720,287 A | 2/1998 | Chapelon et al. | |
| 5,730,720 A * | 3/1998 | Sites et al. | 604/27 |
| 5,899,873 A | 5/1999 | Jones et al. | |
| 5,984,893 A | 11/1999 | Ward | |
| 6,046,805 A * | 4/2000 | Kawamura et al. | 356/244 |
| 6,071,238 A | 6/2000 | Chapelon et al. | |
| 6,223,793 B1 * | 5/2001 | Donoughe et al. | 141/338 |
| 6,371,903 B1 | 4/2002 | Blanc et al. | |
| 6,432,069 B1 | 8/2002 | Godo et al. | |
| 6,673,594 B1 * | 1/2004 | Owen et al. | 435/284.1 |

FOREIGN PATENT DOCUMENTS

| | | | |
|---|---|---|---|
| DE | 19509005 | * | 4/1996 |
| FR | 2 750 340 | | 1/1998 |
| JP | 06063127 A | * | 3/1994 |

* cited by examiner

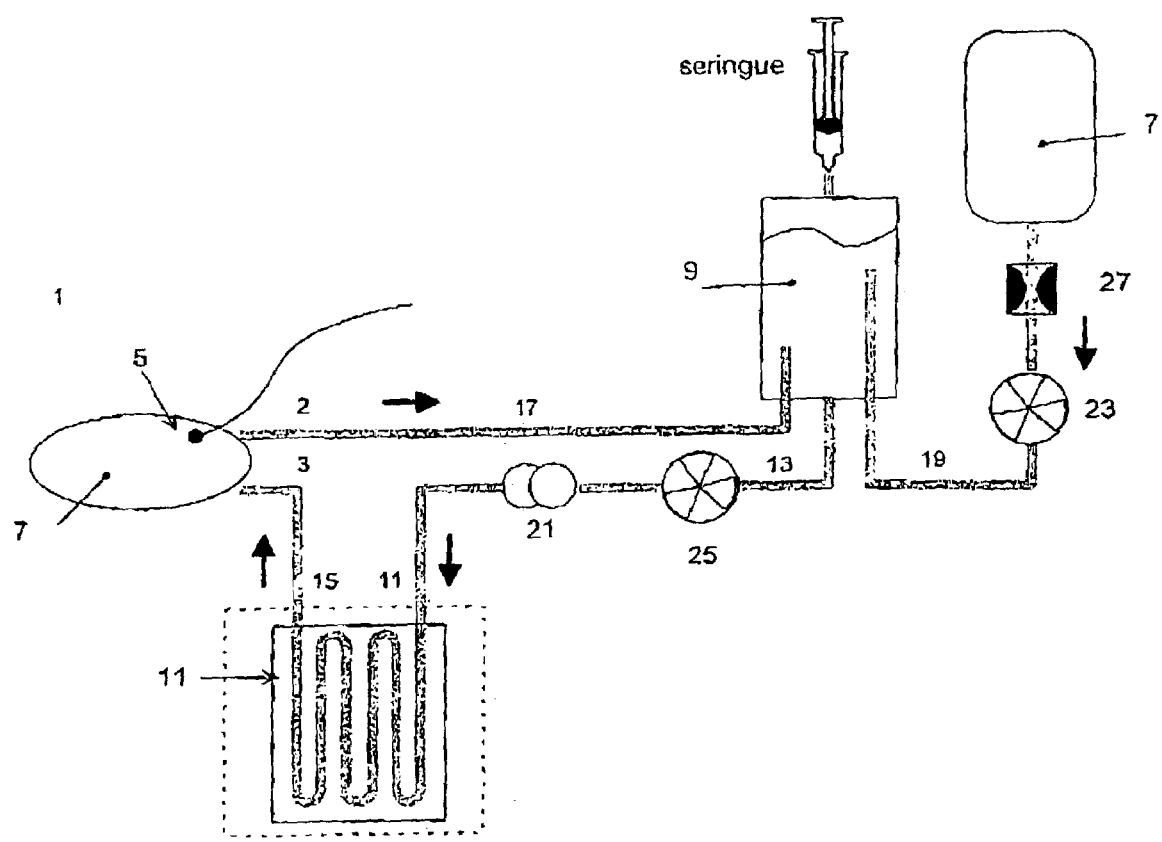

FLUID MANIPULATING SYSTEM FOR THERAPY APPARATUS

The invention relates to systems for manipulating fluids, and more specifically for manipulating fluids used in therapy apparatus. It also relates to a kit (set of preassembled parts) for producing such a system.

U.S. Pat. No. 5,899,873 describes a system for delivering a biological fluid, in this case, a cardioplegia solution for supplying the heart during open-heart surgery. The system consists of a pump which receives, on the one hand, blood coming from an oxygenation machine and, on the other hand, a crystalloid solution coming from a reservoir. The pump mixes these two fluids and transmits them to a heat exchanger; the latter moreover receives a potassium solution, or solutions with additives. Once the fluids are mixed and brought to a suitable temperature, they are then directed toward the patient's heart. The heat exchanger of this document is a single-piece assembly, which provides the functions of temperature control, filtration, gas separation and measuring parameters of the cardioplegia fluid, such as pressure or temperature. In this system, there is no fluid recovery; the flowrate of the pump is adjusted according to the pressure measured by the pressure sensor.

U.S. Pat. No. 5,984,893 describes a system for rapid infusion of blood fluid making it possible to control the hematocrit level of a patient. The system comprises a fluid source and a blood source, in the form of flexible bags capable of being suspended from poles known per se. Two pumps control the flowrate of fluid and of blood. The mixing is carried out in a tubing and is sent to a heat exchanger, a degassifier, a bubble detector and a temperature and pressure sensor. The pumps are controlled by a blood replacement monitor, which monitors the flowrate of the pumps so as to maintain a constant hematocrit level in the patient's blood. The prior art section of this document describes injection devices, comprising a cardiotomy reservoir, a circulation pump, a heat exchanger and a bubble trap.

These two documents show open-circuit systems for injecting a fluid.

U.S. Pat. No. 4,874,359 also shows a system for rapid infusion of blood fluid. Again, two reservoirs for fluid and for blood are provided, the respective outputs of which are mixed in a reservoir. The mixture from the reservoir is supplied to a bubble detector, then to a peristaltic pump with a flowrate sensor. The outlet from the pump is connected to a heat exchanger, then to a bubble trap. The air coming out of the bubble trap is sent to the reservoir, so that the bubble trap can be purged without opening the infuser to the outside. A Y connector fitted with temperature and pressure sensors is provided at the outlet of the bubble trap toward the patient; one outlet from the Y goes toward the patient, and the other outlet is a loop recirculating toward the reservoir.

The system of this document allows fluid to flow, but only before it is injected into the patient.

U.S. Pat. No. 4,186,565 describes a perfusion system for the preservation of organs such as the kidneys. This system comprises a vessel, and a closed fluid circuit; the circuit comprises, in order, a pump, a bubble trap, the organ, an oxygenator, a heat exchanger, and again, the pump. The objective in this document is to supply the organ with fluid, in order to ensure its preservation in the solution of the vessel.

The various systems are not suitable for the manipulation of fluid for an apparatus in the fluid is not intended to be injected, but must be recovered or circulated. An example of such an apparatus is the apparatus for treating, by hyperthermy, the prostate, which is marketed by the applicant under the trademark Ablatherm, and which is described in patent applications FR 93 09 158 and FR 96 08 096.

This apparatus has a transducer for therapy by emission of focused ultrasound, which is placed in a rectal probe with a flexible envelope. The probe has one inlet and one outlet for fluid. The fluid flowing through the flexible envelope of the probe cools the therapy transducer, also cools the rectal wall and finally, transmits ultrasound from the transducer toward the tissue. In the current embodiment of the apparatus, the flexible envelope is a small single-use balloon. This is fastened to the probe before it is introduced into the patient. The fluid inlet and outlet of the probe, which are located in that part of the probe which remains outside of the patient, are in fluid communication with the inside of the small balloon and make it possible to inflate this small balloon to a greater or lesser degree.

The invention is applicable to the manipulation of fluid for this apparatus. It proposes a solution which makes it possible to resolve one or more novel problems as follows:
 isolate the fluid from the environment—patient or outside;
 monitor the amount of fluid applied to the apparatus;
 recover the fluid after use;
 avoid bubbles; and
 monitor the temperature, the flowrate and the pressure of the fluid.

More generally, the invention is applicable to other types of devices or apparatus than that given by way of example—a probe with a therapy transducer—and for which it is desired to monitor the distribution of a fluid to be recovered. It is generally applicable to monitoring the application of a fluid to a device which has a fluid inlet and a fluid outlet.

The solution of the invention is simple and effective; it makes it possible to solve the problems mentioned above.

The invention proposes a fluid manipulating system; it also proposes a fluid manipulating kit for an apparatus having a fluid inlet and outlet.

According to the invention, the fluid manipulating system comprises a fluid reservoir, a bubble trap connected to the reservoir, a heat exchanger and an apparatus forming, with the bubble trap, a closed fluid circuit, and a pump making the fluid flow in the closed circuit.

In one embodiment, the pump is located upstream of the apparatus in the flow direction of the fluid.

It is also preferable that the heat exchanger is upstream of the apparatus in the flow direction of the fluid.

Provision may be made for a valve between the bubble trap and the reservoir, a flowrate sensor between the bubble trap and the reservoir, and/or a flowrate sensor on the closed circuit.

In a preferred embodiment, the apparatus is an ultrasound therapy probe. The fluid is then a coupling and cooling liquid.

The invention also provides a kit for manipulating fluid toward an apparatus having an inlet and an outlet, comprising a fluid reservoir, a bubble trap, a heat exchanger and tubings for connecting the reservoir to the bubble trap, and for forming a closed circuit between the bubble trap, the heat exchanger and the apparatus.

In a preferred embodiment, the reservoir is sealed and flexible. Other features and advantages of the invention will become apparent on reading the following description of embodiments of the invention, given by way of example and with reference to the appended drawings, the single FIGURE of which shows a schematic representation of a fluid manipulating system according to the invention.

The FIGURE shows schematically an apparatus 1, which has a fluid outlet 2 and a fluid inlet 3, and through which the fluid has to be manipulated. In the example, the fluid outlet 2 operates above the fluid inlet, so as to improve the removal of bubbles with the fluid current. The apparatus is, for example, a rectal probe fitted with an inflatable flexible envelope, like the one mentioned above. In this case, the fluid is for example the ultrasonic coupling fluid described in French patent application 9903738 by the applicant.

Hereinbelow, the invention is described only with reference to this example, although it is clear to a person skilled in the art that it is more generally applicable to any type of apparatus having a fluid inlet and a fluid outlet.

Apart from the apparatus, the fluid manipulating system of the invention has a fluid reservoir 7. The outlet from the fluid reservoir is connected to a bubble trap 9. This bubble trap is part of a closed circuit comprising a heat exchanger 11 and the apparatus 1.

More specifically, one outlet from the bubble trap 9 is connected by a tubing 13 to one inlet of the heat exchanger 11. One outlet of the heat exchanger is connected by a tubing 15 to the inlet of the apparatus, and the outlet of the apparatus is connected by a tubing 17 to an inlet of the bubble trap 9. In this description, a person skilled in the art will understand that the terms "inlet" and "outlet" denote orifices of various elements and in fact are only differentiated in practice by the flow direction of the fluid. Thus, in the example, the bubble trap may have three orifices, connected firstly to the tubing 13, secondly to the tubing 17 and finally to a tubing 19, the other end of which is connected to the reservoir. A person skilled in the art will also understand that the tubings may be made as one piece with some of the elements and, for example, the heat exchanger could be made as one piece with the tubings 13 and 15.

The FIGURE also shows a pump 21 making it possible to circulate the fluid through the closed circuit formed by the bubble trap, the heat exchanger and the apparatus. In the assembly in the example, this pump is located between the bubble trap and the heat exchanger.

Flowrate detectors 23 and 25 are also shown in the FIGURE, placed respectively between the reservoir and the bubble trap, and between the bubble trap and the pump. The FIGURE further shows a valve 27, located between the reservoir and the bubble trap. Finally, a temperature sensor 5, placed in the apparatus, whose function will become apparent in the rest of the description, is shown in the FIGURE.

The preferred embodiments of the various elements of the FIGURE are now described, before describing the operation of the invention.

The function of the reservoir 7 is to contain the fluid to be manipulated. It preferably consists of a sealed flexible pouch. Thus, it can be emptied without having to have an air inlet; this makes it possible to prevent any risk of the fluid being regassed, and further makes it possible for the volume to be monitored more simply. The fluid is preferably sterile for medical applications, but it could also be a corrosive fluid in other applications.

One advantageous solution for connecting the reservoir to a tubing is to provide an orifice fitted with an end piece which is easy to pierce on introduction of a tubing. Such an end piece is known in medical applications and is not described in further detail. Preferably, a chamber is located between the end piece and the tubing, making it possible to trap any bubbles.

In the example, a valve is provided at the outlet of the reservoir, on the tubing 19 between the reservoir and the bubble trap. The valve may, for example, consist of a member for gripping the tubing, making it possible to stop the fluid flow, without, however, coming into contact with the fluid. The function of the valve is simply to allow the fluid connection between the reservoir and the bubble trap to be interrupted.

The bubble trap 9 may operate according to any principle known per se. In the simplest configuration shown in the FIGURE, the bubble trap is simply a rigid envelop located at a high point of the circuit, the orifices of which are in the low part. The bubbles are then trapped in the upper part of the bubble trap. Refinements may also be added, for example to ensure that the fluid flow in the bubble trap promotes degassing. In the embodiment of the FIGURE, the bubble trap is in form of a rigid cylinder made of transparent plastic with a height of about 100 mm and a diameter of about 25 mm. In its bottom are located three orifices extended inside the cylinder by tube portions. One of these tubes rises up to 40 mm from the bottom, the other to 20 mm, while the third is flush with the bottom. The tubing 19 is connected to the first orifice, the tubing 17 to the second and the tubing 13 to the third. Thus, the air present in the bubble trap is not sucked into the circuit, while the bubbles contained in the circuit are trapped. The fact that the tubing 19 is connected to the orifice having the highest tube portion prevents the bubble trap being emptied completely into the reservoir, even if, during pump operation, the reservoir is placed below the bubble trap.

Provision may be made for a valve located in its upper part of the bubble trap to allow the bubble trap to be emptied. This valve makes it possible to extract air from the bubble trap, but also to add or remove liquid to or from the circuit. Advantageously, this system has the safety feature of only being able to be activated by inserting a syringe, as shown in the FIGURE. Consequently, the valve cannot in any case remain in a position open to free air, which maintains the isolation of the fluid. Such a safety device is known per se, and is available commercially under the name "syringe activated check valve".

The pump 21 circulates the fluid in the main circuit. It is preferably of peristaltic type, and tubings are inserted therein. This makes it possible for the fluid not to be contaminated and, conversely, prevents the fluid interacting with the stationary elements of the apparatus. This further increases the isolation between the fluid and the environment.

The heat exchanger 11 is, in the exemplary embodiment of the FIGURE, formed by a coil in which the fluid flows and which is immersed in a thermostatic bath. It may be manufactured from a flexible material, such as PVC. More simply, it may also be constructed from a tubing or part of a tubing which is immersed in the thermostatic bath. In the example of a hyperthermy apparatus, the fluid is cooled and the thermostatic bath is, for example, kept at a temperature close to 5° C. such that the temperature in the envelope of the probe remains close to 15° C., the flowrate being about 8 liters/hour. In all cases, the function of the heat exchanger is to act on the temperature of the fluid which passes through it. In the example, this temperature is measured at the level of the apparatus 1, by means of a temperature sensor 5. Its sensitive element is located in the region to be monitored, for example in the envelope of the probe close to the fluid outlet or else in the outlet tubing. This position of the sensor is advantageous in that it also makes it possible to detect a flow fault, by heating of the fluid. The sensor may be connected to an electronic measuring apparatus. It will be noted that the sensor is not essential to the operation of the invention, but simply allows better monitoring of this operation.

The flowrate detectors also allow better monitoring of the operation of the system of the invention, and may also be removed. Advantageously, a flow meter with blades can be used for one or other of the flowrate detectors. Its rotation is controlled by an optical barrier which is connected to an electronic device capable of detecting and of counting the pulses, which correspond to the movement of the blades. The detection may be of the "all or nothing" type or it is possible to measure the rotation rate of the blades and thus calculate the flowrate of the fluid.

The operation of the system is now described.

First Filling of the Apparatus

Initially, no fluid is present in the circuit. The system is assembled: The tubings are mounted so as to form the closed circuit, the tubings are placed in the peristaltic pump and the reservoir is connected to the bubble trap. If required, the flowrate detector or detectors are placed facing the optical barrier. The heat exchanger is placed in the thermostatic bath. In the case of Ablatherm, the small flexible balloon is placed around the probe.

To fill the circuit, the reservoir containing the fluid is placed in the high position—that is to say above the bubble trap. It is pierced in its low part with the perforator. If present, the valve is opened. The fluid flows by gravity into the tubings toward the bubble trap, and from the latter toward the apparatus 1. In order that the filling be carried out correctly and quickly, the reservoir is, for example, located at a given height H above the apparatus, typically about 1 m.

The emptying of fluid from the reservoir toward the circuit can be interrupted at any time, by actuating the valve 27. It will also be noted that the reservoir may contain exactly the necessary fluid. Or else its content may be limited so that the apparatus, if it is extendable, cannot burst.

When the reservoir 7 is emptied, either completely or down to a predetermined mark, the circulation pump 21 is started. This causes the fluid to flow through the closed circuit. The air contained in the tubing 13, 15, 17, in the apparatus 1 and in the heat exchanger 11 is thus made to flow with the fluid. It is sucked out of the apparatus, in particular because of the position of the outlet of the apparatus, and is trapped when it passes into the bubble trap. In the case of Ablatherm, all the air which may have been contained in the apparatus, between the small balloon and the probe, is especially removed. After a few seconds of flowing, all the residual air in the tubings and in the apparatus is collected in the bubble trap. Preferably, the air present in the bubble trap is completely extracted by means of the syringe. Extracting air from the bubble trap makes it possible to adjust, with accuracy, the exact volume of fluid in the closed circuit, and therefore, in operation, the amount of fluid in the apparatus, knowing the volume of the bubble trap, of the heat exchanger and of the various elements of the circuit.

The apparatus is now filled with the, help of the reservoir, with no possible contamination of the fluid, and without the fluid being in contact with the environment. As mentioned above and explained now in detail, by means of the invention, it is easily possible to adjust the fluid volume in the circuit.

Deflation of the Apparatus

After filling the apparatus and purging the residual air, it may be necessary to partially empty it. For example, in the case of Ablatherm, it is necessary to deflate it before inserting the rectal probe into the patient. This operation is carried out by lowering the reservoir, if necessary after having opened the valve. The pump is stopped since the flow direction is the reverse of the emptying direction. The reservoir is again filled with fluid from the apparatus and from the bubble trap, which are emptied. When the reservoir contains the desired amount of fluid, the valve is closed. Partial deflation is therefore possible. It will be noted that no bubbles are introduced into the circuit during this operation.

Inflation of the Apparatus

The apparatus may also be filled with a known, controlled volume of fluid (typically 150 $cm^3$ in the apparatus example given above) to prevent its bursting.

The reservoir is then replaced in the high position, if appropriate after having opened the valve, and the coupling liquid again fills the apparatus. Controlling the filling volume is even simpler if the reservoir has a volume such that, when it is empty, the apparatus is filled with the correct amount of fluid (150 $cm^3$ in the example). Since all these fluid transfers are always carried out with the same volume of fluid, the final volume of the apparatus at the time of treatment is always under control. The pump may be actuated, either to accelerate the filling or to increase the pressure in the apparatus, within the limit of the fluid volume contained in the reservoir.

The valve placed on the tubing located between the reservoir and the bubble trap thus makes it possible to deliberately reduce the fluid volume contained in the apparatus. In the case of Ablatherm, some patients have narrow rectal ampullas (for example, following radiotherapy treatment), and the valve thus provides better control of the fluid volume in the circuit and therefore of the volume of the rectal probe. The flowrate sensor 23, if it exists, may make it possible to control the amount of fluid injected in the circuit.

Fluid Flow

In normal operation, the fluid flows in the closed circuit comprising the apparatus 1, the bubble trap 9 and the heat exchanger 11. Thus the volume of the apparatus is constant. The absence of a valve on the tubings moreover has the advantage of preventing poor handling during installation (poor connection) or in use (valve left open). In the latter case, a leakage of fluid or an intake of air could take place and the apparatus could be emptied or filled in an uncontrolled manner. In the case of Ablatherm, leakage from the apparatus could cause a serious rectal lesion because of a considerable increase in temperature. The absence of a valve on the closed circuit forms a noteworthy safety element of the invention. The temperature of the fluid may be continuously controlled, if a temperature sensor is available. Preferably, the flow is also controlled, by means of the flowrate sensor 25.

The residual bubbles and those formed in the apparatus—in the example of Ablatherm, these bubbles are caused by the action of the ultrasound on the coupling fluid—are collected in the bubble trap during treatment such that the fluid does not become filled with air again. The volume of bubbles formed in the apparatus is low compared to the total volume of fluid, and it can be considered that the fluid volume in the circuit is constant.

Purging the Apparatus

To empty the apparatus and the tubes, the procedure is as for deflating. The fluid is recovered in the reservoir.

The operation of the invention, as described above, makes the following advantages apparent. The invention makes it possible to provide flow and temperature control of the fluid. In the case of use with therapy transducers, it ensures the flow and cooling of the fluid acting as a coupling fluid around the transducer and opposite the tissue interface. In the medical field, it is preferable to have a consumable and closed system: As has been seen, the invention allows the apparatus to be filled or emptied, with no external contact. Thus, it is ensured that the fluid remains aseptic, which prevents any problem if it comes into contact with tissue.

The invention allows fast and simple replacement of the constituents of the system, and especially of the tubings, of the bubble trap or indeed simple changing of the reservoir.

The invention makes it possible to solve the problems mentioned above. The fluid may be isolated from the environment. In the example, the apparatus surrounding the transducers and in contact with the tissue interface may be filled with a special fluid, whose conservation requires precautions. For example, in the medical field, this fluid will be sterile. Again, for example, in the acoustic field, this fluid will be purged of air. In other fields, the fluid will be corrosive. Before use, the fluid may be contained in the sealed reservoir 7. Preferably, this reservoir contains a large enough measure for one use. After use, the fluid may be recovered, without risk of overflowing, and still without risk of contact.

The fluid volume may be known at any time; it is also possible to vary it at will. The bubbles from the apparatus and tubings may be removed from the closed circuit. The fluid contained in the apparatus may be cooled or heated, to a controlled temperature. In the example, the function of cooling the rectal wall is critical for safety and its performance can be controlled under any circumstance.

Furthermore, the following particular advantages will be noted: The arrangement of the pump on the circuit (upstream of the apparatus, downstream of the connection of the bubble trap 9 to the reservoir) prevents the apparatus from emptying should a tubing be pinched, whatever the location where this pinching takes place.

This is because the apparatus cannot be filled and burst if the reservoir contains exactly the required volume, when the reservoir is full, there is no longer fluid in the reservoir. If the tubing is pinched between the reservoir and the apparatus, the reservoir is evacuated under the action of the pump. If, in the circuit, there is a safety valve, it advantageously holds this low pressure so that air does not enter into the circuit, which would risk bursting the apparatus.

The valve makes it possible to prevent inopportune emptying of the apparatus into the reservoir, should the reservoir be inadvertently moved to a position lower than the apparatus or than the bubble trap, during treatment. The position of this valve on the tubings (between the reservoir and the bubble trap) cannot lead to defective operation whether it is open or closed. Even in the absence of a valve, the extension of the tube connected to the tubing 40 in the bubble trap ensures that the bubble trap cannot be completely emptied, and therefore that there is always fluid flowing in the apparatus; in the case of Ablatherm, this provides protection of the rectal wall of the patient under all circumstances.

The invention also relates to a fluid manipulating kit for such a system. The kit is in the form of a blister, closed by a membrane of the "Tyvek" (registered trademark) type, that the user can fit onto a rigid mechanical support mounted on the Ablatherm. The kit comprises a fluid reservoir, a heat exchanger, a bubble trap, and tubings to connect these various elements. Other elements (small disposable balloon to be placed around the probe, ligature to fasten the small balloon, acoustic coupling gel, optical reflector for detecting patient movement, syringe) may also be part of the kit but are not described in this document. This kit makes it possible to replace the circuit elements in contact with the fluid after use. It is then possible to use a new sterile apparatus, and thus to limit as much as possible the risk of nosocomial infections.

Of course, the present invention is not limited to the exemplary embodiments described and shown, but it is capable of many variants accessible to the person skilled in the art. Thus it is possible for the invention to be applied to other apparatuses. The position of the heat exchanger could vary in the circuit, and it could be at the outlet of the apparatus; however the position upstream of the apparatus makes it possible to limit heat losses in the circuit. The preferred position of the pump is shown in the FIGURE; the pump could also, even if it is less advantageous, be between the heat exchanger and the apparatus, or else between the apparatus and the bubble trap. Similarly, the preferred position of the flowrate detector is shown in the FIGURE; this detector could also be placed downstream of the pump. However, its position upstream of the pump makes it possible to check the integrity of the circuit—absence of pinching or of leaks in the small balloon and its return circuit—and therefore offers increased safety of operation.

The devices for controlling the system have not been described in detail above. Provision may be made for the sensors and the pump to be controlled by the same control device, which may be that of the apparatus.

The invention claimed is:

1. A fluid manipulating system, comprising:
a bubble trap;
a heat exchanger;
an ultrasound therapy probe configured to receive fluid flow therethrough;
the ultrasound therapy probe, the bubble trap, and the heat exchanger forming a closed fluid circuit;
a pump providing fluid flow in the closed fluid circuit; and
a fluid reservoir external to said closed fluid circuit and connected to said bubble trap; and
wherein the bubble trap includes first and second orifices in fluid communication with the closed fluid circuit, and includes a third orifice in fluid communication with the reservoir for receiving fluid from the reservoir whereby fluid from the reservoir is injected into the closed fluid circuit.

2. The system according to claim 1, wherein the pump is located upstream of the ultrasound therapy probe in a direction of flow of the fluid.

3. The system according to claim 1, wherein the heat exchanger is upstream of the ultrasound therapy probe in a direction of flow of the fluid.

4. The system according to claim 1, further having a valve between the bubble trap and the reservoir.

5. The system according to claim 1, further having a flowrate sensor between the bubble trap and the reservoir.

6. The system according to claim 1, further having a flowrate sensor on the closed circuit.

7. The system according to claim 1 wherein the bubble trap includes a syringe activated valve.

8. The system according to claim 1 further including a temperature sensor operatively coupled to the ultrasound therapy probe.

9. The system according to claim 1, wherein the fluid reservoir is flexible.

10. The system according to claim 1, wherein the heat exchanger is located upstream of the ultrasound therapy probe and downstream of the pump in the direction of fluid flow.

11. The system according to claim 1, wherein the heat exchanger is a flexible envelope.

12. A closed fluid system comprising:
a multiple-port bubble trap;
a heat exchanger;
a fluid receiving ultrasound therapy probe;
conduits interconnecting the bubble trap, the heat exchanger and the ultrasound therapy probe to form a closed fluid flow circuit;
a fluid reservoir external to said closed fluid circuit and in at least intermittent flow communication with one of the ports of the bubble trap to fill the circuit with a first quantity of fluid while maintaining the closed circuit, and, to withdraw at least part of the fluid from the circuit while maintaining the closed circuit.

* * * * *